United States Patent [19]

Wortberg

[11] Patent Number: 4,573,216

[45] Date of Patent: Mar. 4, 1986

[54] IMPACT DISSIPATOR

[76] Inventor: Walter Wortberg, Buschhauser Weg 13b, 5880 Ludescheid, Fed. Rep. of Germany

[21] Appl. No.: 512,020

[22] Filed: Jul. 8, 1983

[30] Foreign Application Priority Data

Jul. 10, 1982 [DE] Fed. Rep. of Germany ... 8219790[U]
Feb. 17, 1983 [DE] Fed. Rep. of Germany ....... 3305408

[51] Int. Cl.⁴ ............................................ A41D 13/00
[52] U.S. Cl. ................................................ 2/2; 2/22; 264/222; 128/132 R
[58] Field of Search ...................... 2/2, 16, 22, 24, 412, 2/413; 128/132 R, 522; 264/222

[56] References Cited

U.S. PATENT DOCUMENTS

| | | | |
|---|---|---|---|
| 2,889,830 | 6/1959 | Raymond | 128/522 |
| 2,935,130 | 9/1960 | Scholl | 128/153 |
| 3,322,873 | 5/1967 | Hitchcock | 264/222 |
| 3,526,221 | 9/1970 | Garber | 128/132 R X |
| 3,990,440 | 11/1976 | Gaylord, Jr. | 2/24 X |
| 4,067,063 | 1/1978 | Ettinger | 2/413 X |
| 4,151,613 | 5/1979 | Rhee | 2/2 |
| 4,292,263 | 9/1981 | Hanrahan et al. | 2/24 X |

FOREIGN PATENT DOCUMENTS

| | | |
|---|---|---|
| 836552 | 3/1952 | Fed. Rep. of Germany . |
| 1902645 | 7/1964 | Fed. Rep. of Germany . |
| 7715810 | 9/1977 | Fed. Rep. of Germany . |
| 8219790 | 10/1982 | Fed. Rep. of Germany . |
| 998525 | 1/1952 | France . |
| 1002955 | 2/1965 | United Kingdom . |

Primary Examiner—Peter Nerbun
Attorney, Agent, or Firm—Schwartz, Jeffery, Schwaab, Mack, Blumenthal & Evans

[57] ABSTRACT

An impact dissipator for the protection of bones and organs of the human body from impacts or falls. The dissipator is bell-shaped and has an outer layer which consists of an elastic rubber substance. Within the shell-like outer layer a viscous fluid layer is located, which is bonded thereto, with the fluid layer forming a skin-friendly adhesive layer adapted to contact and conform to the area being protected.

7 Claims, 10 Drawing Figures

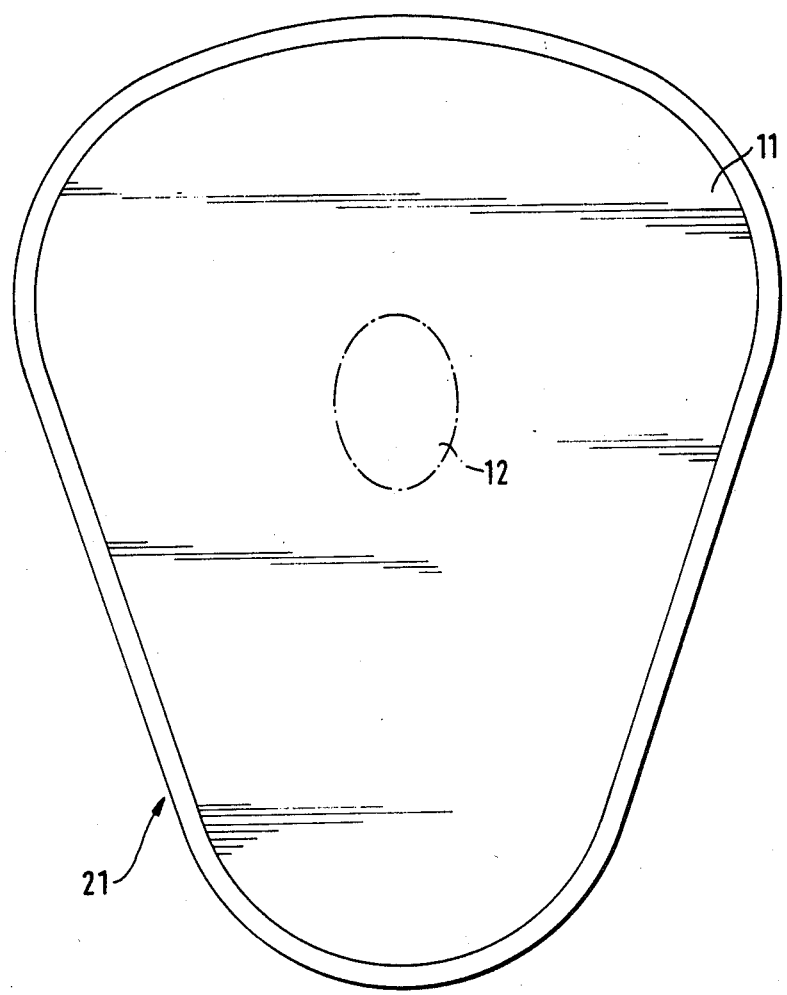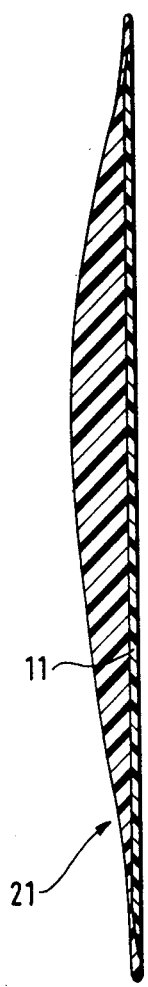

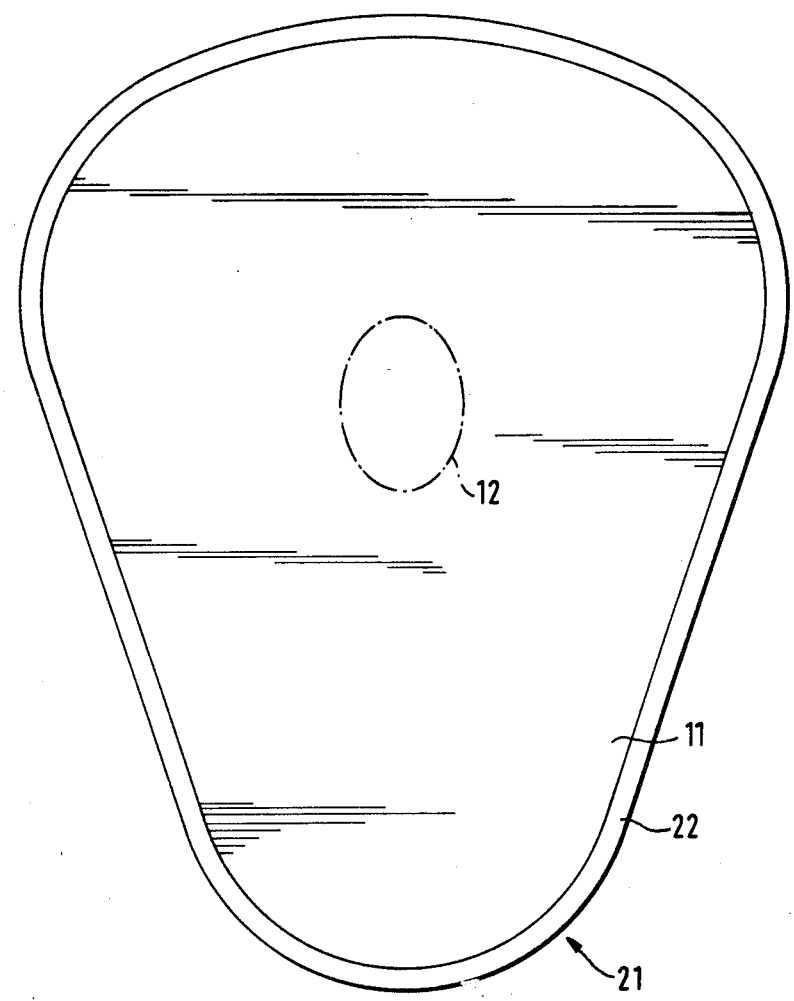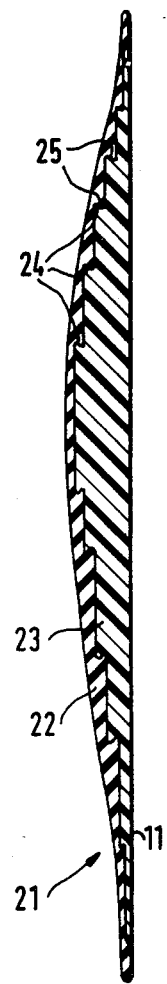

IMPACT DISSIPATOR

BACKGROUND OF THE INVENTION

The invention concerns an impact dissipator to protect the human body.

The field of application of the invention consists of the protection of endangered bones and joints. In older persons, the area of the hip is particularly endangered. A further application of the invention is the protection of organs.

In older persons the fracture of the femur near the hip joint is the most frequent bone fracture. Investigations show clearly that the number of these fractures of the femur close to the hip joint increases with the age of the person. Per-Axel Alffram in "An Epidemiologic Study of Cervical and Trochanteric Fractures of the Femur in an Urban Population", Acta orthop. scand. Supplementum No. 65, 1964, Malmo, showed unambiguously that the most frequent cause of such fractures of the femur are light falls. The inventor's own investigation confirmed these findings.

The occurrence of such fractures of the femur near the hip joint results in long stays in a hospital and an extended duration of the illness for the persons afflicted. Mortality is relatively high. In the Federal Republic of Germany, the number of fractures of the femur in older persons amounts to approximately 40,000 per year. Fractures of the femur of this type represent not only a problem of preventive medicine, but also of social medicine.

For orthopedic purposes, pressure cushions or pads of foam or sponge rubber are known, see, for example, DE-GM No. 19 02 645 or DE-GM No. 77 15 810. Such pressure cushions are intended to apply pressure to or provide support for a certain skin or tissue area. Pressure cushions of this type are not suitable for use as impact absorbers to absorb as much impact or fall energy as possible.

SUMMARY OF THE INVENTION

It is the object of the present invention to provide an impact dissipator capable of containing and absorbing the highest possible proportion of an impact or fall. This object is attained according to the invention by providing an impact dissipator having the following characteristics:

(a) a bell-shaped cross section;

(b) a bottom side which contacts the skin and which has an adhesive layer friendly to the skin;

(c) an outer layer on the side which preferably consists of an elastic rubber substance;

(d) within the shell-like outer layer there is a layer of a viscous fluid, which is integrally bonded to the outer layer by chemical bonds in the boundary layer.

The adhesive layer is protected prior to use by a removable covering sheet. When used to protect the hip joint, the impact dissipator is adhesively bonded with its base surface to the skin approximately in the longitudinal direction of the femur, with the area of the greatest thickness covering the trochanter major or greater trochanter. The impact neutralizer has a thickness of approximately 20 to 50 mm, preferably 20 to 40 mm, in the area of greatest thickness. The dimension of the greater trochanter is 6 to 10 cm. The base area of the impact dissipator is preferably 16 cm. in width and 20 cm. in the longitudinal direction of the femur.

The adhesive layer assures seating on the skin without slipping and contributes to the attenuation of stresses. It was discovered that the stiffness of silicone rubber is force-dependent. Investigations have shown that the impact force acting on the greater trochanter in the case of a fall may be reduced by the impact dissipator to approximately 30 to 45% of the impact force that would be effective without the impact dissipator. The impact force is thus reduced to a point where normally no fracture would occur in the area of the femur in the vicinity of the hip joint. As the fluid of the fluid layer is incompressible, in case of an impact the fluid layer yields and displaces the elastic rubber layer. In the course of the elastic restoration this leads to the delayed release of the impact energy. A high damping effect is thereby obtained.

The impact dissipator for the area of the femur near the hip joint may also be designated or serve as an auxiliary pad. In this application the impact dissipator has an oval configuration.

In a further development of the invention, the outer layer consists of a cross-linked silicone rubber and the fluid layer of a silicone rubber without cross linking. The cross-linked silicone rubber has elastic rubber properties and the partially cross-linked silicone rubber fluid-like characteristics.

The invention further proposes that the fluid layer be exposed on the bottom side of the impact dissipator and form the adhesive layer. The fluid layer is thus utilized as the adhesive layer.

The cross-linked silicone rubber is soft and yielding. Its hardness may be regulated within a wide range in keeping with the specific application by means of the proportion of the catalyst added during processing. Silicone rubber is readily worked into any particular shape. It is highly insensitive with respect to temperature variations, detergents and abrasion. There is no material fatigue, it does not absorb humidity, and is flexible and tear resistant. The rubber has good insulating properties against the cold and heat, and is dermatologically compatible. No allergies are known and no eczema or chaffing occur. Silicone rubber is friendly to the skin and rapidly adapts itself to the temperature of the body.

As the result of the adhesive effect of the fluid layer, the impact dissipator adheres directly to the skin so that it may be worn permanently, even during the night. This provides protection against falling from the bed, which is important for older persons. As it is not necessary to remove the impact dissipator, it may be worn during hygienic and sanitary activities. It offers protection during bathing and the use of toilets. The adhesive layer assures the fixation of the impact dissipator on the skin, so that it cannot shift. This contributes further to the attenuation of impacts.

The partially cross-linked silicone rubber of the fluid layer is bonded chemically to the silicone rubber layer of the outer layer in an integral manner. In this configuration of the impact dissipator the skin-friendly properties of silicone rubber are fully effective. The fluid-like silicone rubber of the self-adhering layer adapts itself to the profile of the skin and in particular fills the pores of the skin, so that an extraordinarily strong adhesion of the impact dissipator is assured. This is of great importance for the damping effect in relation to the stress of a fall.

The invention further provides that the thickness of the adhesive layer amounts to from a few mm to 40 mm, and the total thickness of the impact dissipator from 20 to 50 mm. This configuration results in the fluid layer itself absorbing a large proportion of the energy of a fall, transmitting it to the outer layer. The energy absorbed is released with a delay. This configuration of the impact neutralizer, due to its two-component structure, i.e. an extraordinarily soft, fluid-like fluid layer of partially cross-linked silicone rubber and an elastic rubber outer layer of cross-linked silicone rubber, assures a high damping effect.

In a further development of the invention it is provided that the fluid layer has steps with undercuts at its circumference. An especially favorable damping structure is thereby obtained. The steps have the effect of disk springs.

The invention further provides for the impact dissipator to contain one or more pore-like air chambers. This affects attentuation properties favorably.

In a further development of the invention, the bottom side of the impact dissipator has a concave recess for use in the area of the hip, in the vicinity of the greater trochanter. This facilitates the alignment and fastening of the impact dissipator in its application to the body of the wearer.

For fitting to the female and male anatomy and to different body dimensions, the impact dissipator may be stocked in different sizes. It may be assumed that a few sizes, for example four, would be adequate.

The impact dissipator thus offers a high measure of protection against fracture injuries in the area of the femur near the hip joint. Further possible applications of the impact dissipator are in the protection of the forearm. Fractures of the forearm, especially radial fractures in the vicinity of the wrist, are the second most frequently occurring bone fractures of older persons. They are the most common with children, as a result of sporting injuries during ice skating, roller skating, skate board riding and the like. The impact dissipator can be adhesively bonded to the palm or only to the thumb and the ball of the little finger. A fall on the hand, which is the most frequent cause of radial fractures, may thereby be attenuated.

The impact neutralizer may also be used as a cushion for the coccygeal bone. This provides protection against compression fractures of the vertebral column. The impact dissipator may have in this particular application of use a horseshoe-like configuration, with the two legs of the horseshoe encompassing the anal fold.

The impact dissipator is further suitable for use as a head cushion to protect the forehead, temporal lobe and the occiput. The vault of the cranium may be protected by suitable cross pieces. Such an impact dissipator is appropriate for small children suffering from epilepsy, but also for older children and adults, and persons involved in sports.

The impact dissipator may also be used as a cushion to protect the tibia, especially the tibial crest. The impact dissipator covers the entire tibial crest, and is particularly suitable for soccer and ice-hockey players.

The impact dissipator may further be employed in the protection of internal organs, for example, as a protective belt for the liver, the spleen and kidneys. Motorcycle riders would be able to wear such a belt to particular advantage.

The embodiments of the invention are described hereinbelow with reference to the application drawings.

BRIEF DESCRIPTION OF THE APPLICATION DRAWINGS

FIG. 5 is a front elevational view of a modified form of the impact dissipator;

FIG. 6 is a vertical cross-sectional view of FIG. 5;

FIG. 9 is a further modified form of impact dissipator, and

FIG. 10 is a vertical cross-sectional view of FIG. 9.

DETAILED DESCRIPTION OF THE PREFERRED EMBODIMENTS

Figure 2:
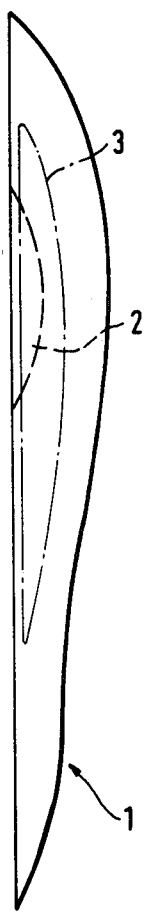
FIG. 2 is a side elevational view of the impact dissipator of FIG. 1.
Figure 1:
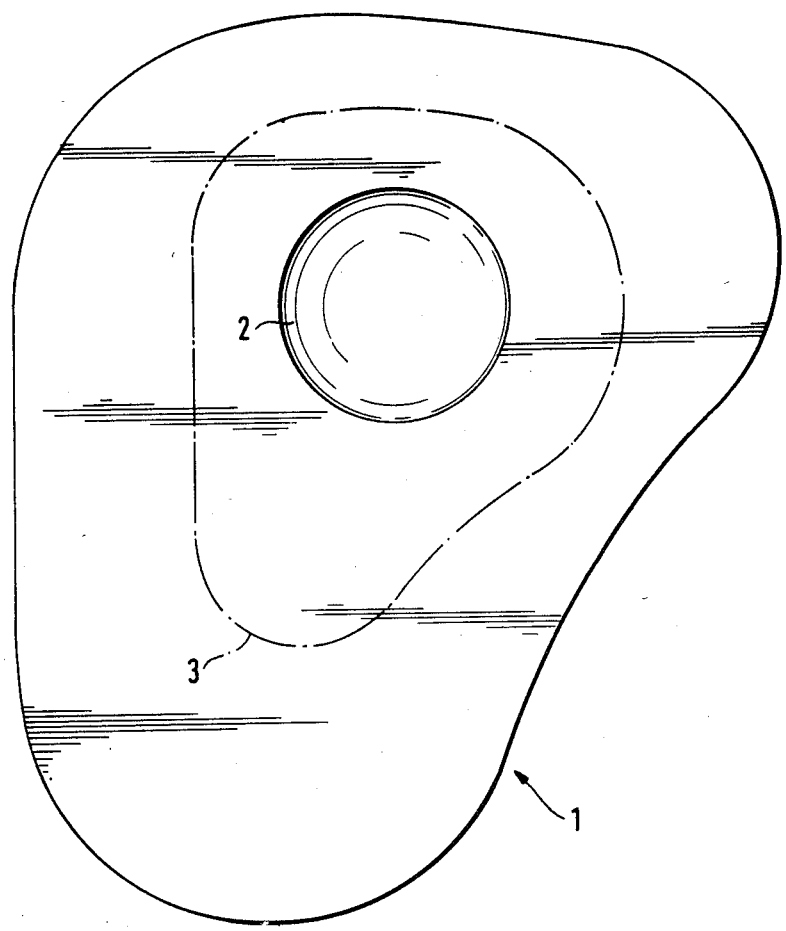
FIG. 1 is an elevational view of the impact dissipator according to the invention.

The impact dissipator generally indicated at 1 in FIGS. 1 and 2 is a cushion of a synthetic plastic with rubber-like properties and has a generally right triangular configuration, the vertical leg in FIG. 1 being approximately twice as long as the leg aligned in the horizontal direction in the figures. This configuration may also be considered an out-of-line oval. This outer configuration may differ from that shown. The impact dissipator consists of a cross-linked silicone rubber, the hardness and thus the damping effect of which may be regulated within a wide range by means of the catalyst added during molding.

The back of the dissipator as shown in FIG. 2 is essentially flat or can be profiled in keeping with the shape of the body, and is intended to contact the skin of the wearer. The back carries an adhesive layer intended to adhere to the skin of the person wearing the device. A concave recess 2 is formed in the back, corresponding to the greater trochanter. The impact dissipator has its greatest thickness over the concave recess. Toward the edge the thickness of the impact dissipator decreases in the manner of a bell or a hill, which is clearly seen in FIG. 2. The highest damping effect is therefore achieved directly over the greater trochanter. The thinner outer areas contribute to the damping effect by preventing a lateral yielding of the material of the impact dissipator. To reinforce this effect, the impact dissipator is bonded directly to the skin of the person wearing it.

Inside the impact dissipator 1, one or several air chambers 3 may be provided as indicated in dashed lines in FIG. 2. The air chamber or chambers may also be in the form of pores.

A further embodiment of the impact dissipator is shown in FIGS. 5 and 6. The impact dissipator is generally indicated at 21 and has an oval outline. In its cross section, the impact dissipator is bell shaped, i.e. the decrease in thickness is initially slight, in the central area the thickness increases strongly, and the profile runs out flat at the edges. In the center area, a support location 12 is indicated in outline, corresponding to the greater trochanter. The latter has a dimension of 6 to 10 cm. The base of the impact dissipator is approximately 16 cm. in width and 20 cm. in height. These values must be adapted to the prevailing body size. The back, support surface of the impact dissipator 21 is essentially flat, and is provided with an adhesive layer 11. The layer 11 may consist of the same silicone rubber material as the body of the dissipator. However, as the result of a smaller catalyst addition to the layer 11, the silicone rubber is only partially polymerized. The adhesive layer is thus bonded chemically to the base body in an integral manner. On the other hand, the adhesive layer is a viscous fluid and has fluid-like properties. Consequently, it will contact the skin of the wearer tightly. Above all, the pores of the skin are filled so that contact by the impact dissipator is tight, thereby providing an extensive protection effect.

The adhesive layer has a thickness of several millimeters, preferably between 3 to 6 mm. As seen in the cross section of FIG. 6, the impact dissipator 21 has a flat, tub-like recess filled by the adhesive layer 11. The total thickness of the impact dissipator is 20 to 50 mm, preferably 20 to 40 mm.

The adhesive is also friendly to the skin, as it consists of skin-compatable partially cross-linked silicone rubber. The impact dissipator according to FIGS. 5 and 6 is essentially symmetrical and may be worn either on the right or the left side.

The impact dissipator shown in FIGS. 1 and 2 is to protect the left hip joint and the area of the neck of the femur. For the right half of the body an impact dissipator representing a mirror image of the first one is provided. In order to have available fitting impact dissipators for all body sizes and for females and males, four different sizes should be sufficient.

Figure 3:
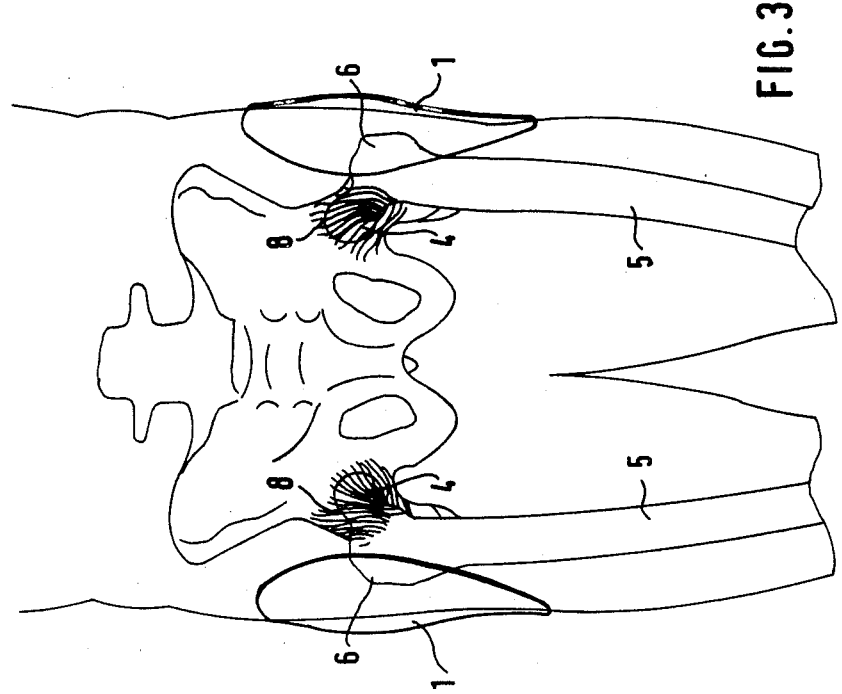
FIG. 3 is a front elevational view of the pelvic area, illustrating the arrangement of the impact dissipator.
Figure 4:
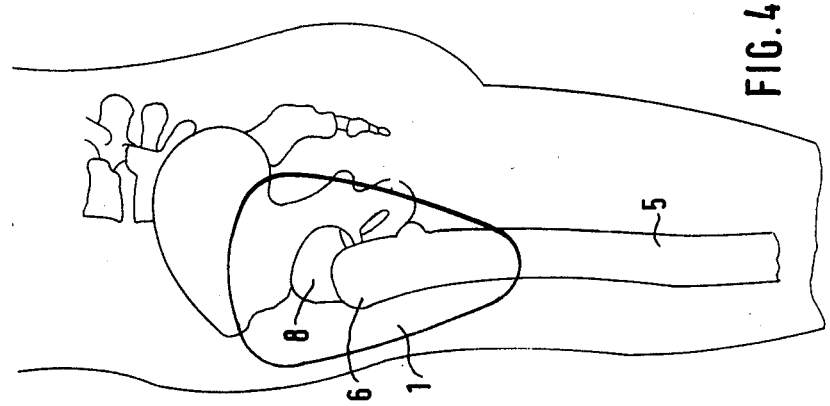
FIG. 4 is a side elevational view of the left side of the body.

FIGS. 3 and 4 show the pelvic area of the human body. In cup 8 of the hip joint the head 4 and the neck of the femur 5 are seated. The greater trochanter 6 projects outwardly from the cup 8 of the hip joint, and is protected by an impact dissipator 1 at both sides of the body. The impact dissipator may be identical for the right and left side of the body or they may be paired. The impact dissipators are applied so that the recess 2 (FIG. 1) or the area 12 (FIG. 5) is located over the greater trochanter. The impact dissipator is fastened to the skin by the fluid-like adhesive layer friendly to the skin of the adherent. The impact dissipator is effective as a protection against falls, as the energy of the fall is absorbed by the yielding, elastic material of the impact dissipator, thereby reducing the stress of the fall. The two-component structure of the impact dissipator with the fluid layer assures a high damping effect.

Figure 7:
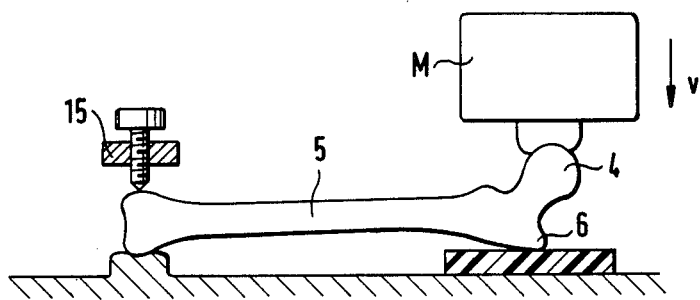
FIG. 7 illustrates an experimental setup for stress testing.
Figure 8:
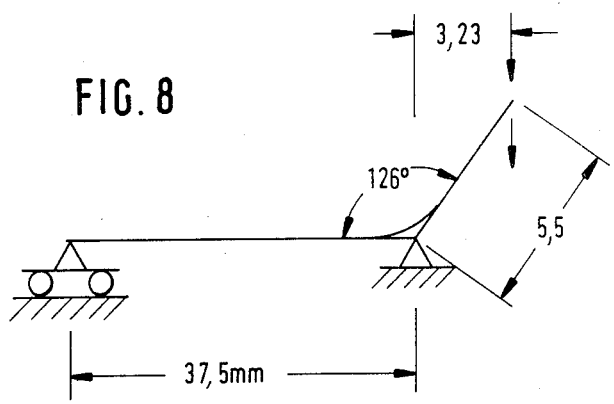
FIG. 8 illustrates the model calculations for the femur.

The effect of the impact dissipator may be estimated by calculation using a linearized theory and verified by experiments. FIGS. 7 and 8 show the corresponding setups and numerical formulations. Referring to FIG. 7, the femur 5 was fixedly clamped at its lower end in a holding fixture 15. The greater trochanter 6 is resting on a protective cushion 21, shown schematically. The head 4 of the neck of the femur is loaded with a mass M, representing the reduced weight of the body. This mass may be moved with a velocity v to simulate a fall.

FIG. 8 shows the dimensions of importance for the strength calculations. The dimensions are entered for a representative femur 5. A consideration of the impact energy both with and without the protective cushion yields the following ratio of the maximum impact forces:

$$\frac{P_m}{P_o} \quad \frac{k_p}{k_F + k_p}$$

wherein $P_m$ is the maximum impact force with the impact dissipator, $P_o$ the maximum impact force without the impact dissipator, $k_p$ the stiffness of the impact dissipator and $k_F$ the stiffness of the femur, including the cartilage of the hip joint and the surrounding skin. The insertion of values obtained from model considerations yields the following:

$P_m/P_o = 0.30$ to $0.45$

The lower value is valid for a small range of forces or approximately 100 daN, and the upper value for an intermediate range of approximately 400 daN. The calculation must be performed as a function of force, as the deformation line of the impact dissipator is progressive. The above cited values indicate that the impact force acting in a fall on the greater trochanter is reduced by the wearing of the impact dissipator to approximately 30 to 45% of the impact force occurring without the impact dissipator. With a thickness of the impact dissipator between 20 and 40 mm, the effect of the impact dissipator is highly beneficial. It is to be expected that the wearing of the impact dissipator would appreciably reduce the number of femurial fractures in the vicinity of the hip joint.

The impact dissipator embodiment according to FIGS. 9 and 10 has a configuration similar to that of FIGS. 5 and 6. The fluid layer 23 of partially cross-linked silicone rubber is built up in steps 24, with the circumferential surfaces being provided with undercuts 25. A cup-like outer layer 22 surrounds the fluid layer 23. The thickness of the fluid layer 23 represents the larger part of the total thickness of the impact dissipator. This impact dissipator has a high absorption capability, as the fluid layer is incompressible and thus displaces the elastic rubber outer layer 22 in the case of an impact or fall. This indicates a storage of the impact energy. The energy is delayed by the elastic rubber outer layer 22 during recovery and released gradually. A high absorption or damping effect is obtained.

I claim:
1. An impact dissipator for protection of the human body, comprising:
   (a) an outer layer consisting of cross-linked silicone rubber;
   (b) an inner viscous-like fluid layer consisting of partially cross-linked silicone rubber integrally bonded to said outer layer at the interface thereof, said inner layer having an adhesive skin-friendly surface adapted to tightly contact the skin of the wearer and conform to the external shape of the body in the region to be protected, and wherein
   (c) said outer and integrally bonded inner layers are generally oval in shape and bell-shaped in cross-section, with the maximum thickness of the bonded layers being in the area contacting the region of the body to be protected.

2. An impact dissipator according to claim 1, characterized in that the inner fluid layer is exposed on the bottom side of the impact dissipator and forms the adhesive surface.

3. An impact dissipator according to claim 1, characterized in that the thickness of the inner fluid layer is up to 40 mm, and the total thickness of the impact dissipator is from 20 to 50 mm.

4. An impact dissipator according to claim 3, characterized in that the inner fluid layer is formed with steps with undercuts at the periphery thereof.

5. An impact dissipator according to claim 1, characterized in that said impact dissipator contains one or more pore-like air chambers.

6. An impact dissipator according to claim 1, characterized in that for application in the area of the hip, the bottom side of the impact dissipator has a concave recess for accommodating the greater trochanter of the hip joint.

7. An impact dissipator according to claim 6, wherein said concave recess is located generally in the area of greatest thickness of said dissipator.

* * * * *